United States Patent
Race et al.

(10) Patent No.: US 7,417,426 B2
(45) Date of Patent: Aug. 26, 2008

(54) COMPACT AND PORTABLE LOW-FIELD PULSED NMR DISPERSION ANALYZER

(75) Inventors: Sean Race, Colts Neck, NJ (US); David Fairhurst, Congers, NY (US); Michael Brozel, Bristol (GB)

(73) Assignee: Xigo Nanotools LLC, Morganville, NJ (US)

( * ) Notice: Subject to any disclaimer, the term of this patent is extended or adjusted under 35 U.S.C. 154(b) by 0 days.

(21) Appl. No.: 11/684,788

(22) Filed: Mar. 12, 2007

(65) Prior Publication Data

US 2007/0210798 A1    Sep. 13, 2007

Related U.S. Application Data

(60) Provisional application No. 60/781,492, filed on Mar. 11, 2006.

(51) Int. Cl.
*G01V 3/00* (2006.01)
(52) U.S. Cl. .................................. 324/303; 324/321
(58) Field of Classification Search .......... 324/300–322
See application file for complete search history.

(56) References Cited

U.S. PATENT DOCUMENTS

| 4,389,613 | A |   | 6/1983 | Brown |   |
|---|---|---|---|---|---|
| 4,480,227 | A |   | 10/1984 | Brown |   |
| 5,602,477 | A | * | 2/1997 | McCarthy et al. | 324/315 |
| 6,278,891 | B1 | * | 8/2001 | Reiderman et al. | 600/410 |
| 6,285,901 | B1 | * | 9/2001 | Taicher et al. | 600/410 |
| 6,479,994 | B1 | * | 11/2002 | Hills et al. | 324/306 |

OTHER PUBLICATIONS

Denkova et al., "Evaluation of the Precision of Drop-Size Determination in Oil/Water Emulsions by Low-Resolution NMR Spectroscopy", Langmuir 2004 20:11402-11413.
Martin et al., "The NMR Mouse: Its Applications to Food Science", Magnetic Resonance in Foods Science:Latest developments, edited by P.S. Belton, Royal Society of Chemistry 2003 pp. 54-61.
Packer et al. "Pulsed NMR Studies of Restricted Diffusion", Journal of Colloid and Interface Sciences 1972 40 (2):206-218.
Shanks et al., "Miniature magnet assembly for NMR-ESR spectroscopy", Am. J. Phys. 1980 48(8):620-622.
Goudappel et al., "Measurement of Oil Droplet Size Distribution in Food Oil/Water Emulsions by Time Domain Pulsed Field Gradient NMR", Journal of Colloid and Interface Sciences 2001 239:535-542.
Stejskal et al., "Spin Diffusion Measurements: Spin Echoes in the Presence of a Time-Dependent Field Gradient", J. Chemical Physics 1965 42(1):288-292.
Van Den Enden et al., "Rapid Determination of Water Droplet Size Distributions by PFG-NMR", Journal of Colloid and Interface Sciences 1990 140(1):105-113.

* cited by examiner

*Primary Examiner*—Brij B Shrivastav
*Assistant Examiner*—Dixomara Vargas
(74) *Attorney, Agent, or Firm*—Licata & Tyrrell P.C.

(57) ABSTRACT

A compact and integrated portable device is provided for the analysis of dispersions by low-field pulsed NMR including: an NMR probe module, a means for generating radio frequency and magnetic field gradient pulses, a signal processor, and a master controller. Also provided are methods for using the device to measure one or more characteristics of phases or particles comprising a dispersion such as surface area, solid/liquid ratio, particle size, and elemental analysis.

19 Claims, 11 Drawing Sheets

Figure 3: Simple single pulse and collect sequence

Figure 4: Simple spin-echo T2 sequence

Figure 5: Simple spin-lattice relaxation T1 sequence

Figure 6: Self diffusion and emulsion sizing sequences

Figure 7: R2 Simulation for three silica dispersions in water 30nm(red), 60nm (green) and 90nm (blue)

Figure 8: R2 Simulation for three silica dispersions in water 30nm, 60nm and 90nm Figure 9: R2sp Experimental data for a silica dispersion in water Figure 10: R2sp Experimental data for surfactant adsorption at two different solids concentrations in water Figure 11: R2sp Experimental data for three different particles in water: alumina(red), silica(green) and latex (blue) in water

COMPACT AND PORTABLE LOW-FIELD PULSED NMR DISPERSION ANALYZER

This patent application claims the benefit of priority from U.S. Provisional Application Ser. No. 60/781,492, filed Mar. 11, 2006, teachings of which are herein incorporated by reference in their entirety.

FIELD OF INVENTION

The invention relates to a compact and portable instrument for simultaneously or sequential measurement of a range of physico-chemical properties of dispersions utilizing low-field pulsed NMR spectroscopy and methods for its use.

BACKGROUND OF INVENTION

Dispersions especially concentrated dispersions are of obvious wide industrial importance in diverse applications such as foods, coatings, fabricated materials and consumer packaged goods. It is well known that the overall characteristics exhibited by such dispersions are in varying degrees controlled by the basic physical properties of the individual particles comprising the dispersion. These properties include the surface chemistry, size, surface area, volume fraction and shape of the particles making up the dispersed phase. Such basic physical properties are generally optimized for a specific application empirically by manipulation of process and composition until the desired characteristics of the dispersion as a whole are achieved, e.g., stability, viscosity, spreadability.

The optimization process itself and the control of the quality of the optimized dispersions, e.g., paint composition, can be greatly facilitated by being able to measure the basic physical properties of the dispersed and continuous phase(s) in an accurate and reproducible way. Indeed, a host of methods and specialized instruments have been introduced over the last 50 years each having their own range of applications, limitations, and assumptions. For example, these include instruments based on dynamic and static light scattering, electrical properties, and acoustics.

Low-field pulsed NMR has been recognized as a potentially powerful technique for the characterization of dispersions since the pioneering work of Tanner and Stejskal (J. Phys, Vol 42, P288 (1965)) and is now widely used to measure for example the size of water droplets in margarine and food spread compositions. Numerous modifications and improvements in the analysis of the relationship between NMR spectra and the particle or other basic physical properties of a dispersion have appeared in the literature in order to make the technique more accurate and reproducible.

Pulsed NMR is an attractive technique for the characterization of dispersions for a number of reasons. Firstly, it is capable of measuring a number of key physical properties as will be discussed further below. This allows in principle one instrument to perform the function of several more specialized instruments thus streamlining the characterization process and potentially the expense of setting up a characterization lab.

Secondly, pulsed NMR allows the characterization of dispersions without the need for dilution, or special sample preparation. For example, the technique can in principle be applied to dispersions containing solid, liquid or gas dispersed phases, concentrated dispersions, optically opaque dispersions, highly viscous dispersions and dispersions containing multiple dispersed phases.

In spite of its potential advantages, pulsed NMR has not gained broad acceptance as a routine technique for the characterization of broad classes of dispersions. Its main use has been in the characterization of droplet size, water content of water-in-oil emulsions, and oil characterization, e.g., solid/liquid ratio, especially in the food and petroleum industry.

Among the potential reasons for the limited use of NMR in particle characterization is the lack of availability of compact, portable and readily affordable instruments that are specifically designed for dispersion characterization. Currently available instruments tend to be bulky, heavy and expensive.

Furthermore, currently available low field NMR instruments are primarily designed as general purpose instruments. As such these instruments are not optimized for dispersion characterization. Since the science underpinning pulsed NMR is complex, especially the relationships between pulse sequencing, signal acquisition and dispersion characteristics, the task of adapting these instruments for routine analysis is often daunting.

The following patents and publications form a part of the related art:

U.S. Pat. No. 4,389,613 and U.S. Pat. No. 4,480,227 to Brown describe portable pulsed NMR instruments and method of use that are designed to measure fluid flow properties in porous media especially oil field rock samples.

Shanks et al in a publication entitled "Miniature magnet assembly for NMR-ESR spectroscopy" (Am. J. Phys, Volume 48, pp 620-622) describes the evaluation in terms of field strength and field uniformity of the magnet assembly incorporating a sintered $SmCo_3$ pole pieces. The assembly has a field strength of 3.35 kG with a claimed uniformity of +/−13.4 mG.

Martin et al. in a publication entitled "The NMR mouse: Its application to food science" (Magnetic Resonance in Foods Science: Latest developments, edited P S Belton, Royal Society of Chemistry, 2003) describes a low field bench top pulsed instrument based on a one-sided magnet and surface mounted RF coils. The magnet arrangement provides a high but rapidly decaying magnet field adjacent to one of the poles of the magnet.

Packer and Rees report the use of a pulsed magnetic field-gradient spin echo technique for the determination of droplet size distribution in emulsions (J. Colloid and Interface Sci., vol. 40, p206 (1972)).

Van Den Enden et al. describe a protocol for the rapid determination of water droplet size distributions in water-in-oil emulsions by pulsed field gradient NMR utilizing echo attenuation caused by restricted diffusion (J. Colloid and Interface Sci., vol. 140, p105 (1990)).

Goudappel et al. developed a method for measuring oil droplet size in oil-in-water by pulsed field gradient NMR by suppression of the NMR signal from the continuous water phase (J. Colloid and Interface Sci., vol. 239, p 535 (2001)). The accuracy of this technique was subsequently checked by Denkova et al. (Langmuir, vol. 20, p11402 (2004).

SUMMARY OF THE INVENTION

The present invention seeks improvements over the known art.

Among the one or more problems addressed by the present invention is the development of a low field pulsed NMR device specifically tailored to the measurement of dispersion physical properties that is very compact, portable and sufficiently low cost so that it can be used in routine product optimization and quality monitoring.

Another objective of the present invention is to provide a compact and portable low-field pulsed NMR specifically designed and optimized to measure simultaneously or sequentially a range of dispersion properties on the same sample and requiring only a limited number of decisions by the operator.

Another objective of the present invention is to provide a compact and portable low-field pulsed NMR specifically designed and optimized to measure simultaneously or sequentially a range of dispersion properties on the same sample and requiring only a limited number of decisions by the operator in which the components are integrated and housed in a single cabinet.

Yet another objective of the present invention is to provide a method to rapidly measure the total or specific surface area of the dispersed phase in-situ either alone or in combination with other physical properties of the dispersion.

Thus, the present invention relates to a compact and portable instrument for the simultaneous or sequential measurement of a various physico-chemical properties of dispersions utilizing low-field pulsed NMR spectroscopy methods.

In one embodiment, the invention relates to an instrument that includes an integrated system comprising relatively light weight components, efficient, compact yet versatile signal generation, processing and control means that collectively have relatively low power demands. Low power consumption offers the possibility of battery operation, reduces temperature fluctuations in the module, enhances magnetic field stability, electronic component and circuit stability, and minimizes sample thermal fluctuations.

Specifically the instrument is a compact and portable device for the analysis of dispersions by low-field pulsed NMR and comprises: an NMR probe module, a means for generating radio frequency and magnetic field gradient pulses, a signal processor, and a master controller; wherein the device measures one or more characteristics of the phases or particles comprising the dispersion selected from the group consisting of surface area, solid/liquid ratio, particle size, adsorbed surfactant, and elemental analysis; and wherein the device has a total footprint area less than about 0.25 m$^2$, an elevation less than about 0.45 m, a weight less than 20 kg, and an operating power demand less than 500 W but preferably less than 200 W.

In another embodiment the NMR probe module, the means for generating radio frequency and magnetic field gradient pulses, the signal processor and the master controller are integrated and housed in a single cabinet having a total footprint area less than about 0.25 m$^2$, an elevation less than about 0.45 m, a weight less than 20 kg, and an operating power demand less than 200 W 500 W but preferably less than 200W.

In a further embodiment the single cabinet has a total footprint area of less than 0.2 m$^2$, a maximum elevation of less than 0.3 m, and the operating power demand of no more than 150 W.

Another embodiment of the invention is a compact, portable low-field NMR device that is housed in a single cabinet and measures the surface area of various types of dispersions.

Another objective of the present invention is to provide a method to rapidly measure the total or specific surface area of the dispersed phase in-situ either alone or in combination with measurement of other physical properties of the dispersion. This method relies on an understanding of the way the average measured spin relaxation rate constants depends on the relative proportions of bulk and "surface" phases" present in the dispersion.

Specifically, the method for in-situ surface area determination comprises:

i) determining an average NMR relaxation rate constants (spin-spin (2) or spin lattice (1)), $R_1^{ave,ref}$ or $R_2^{ave,ref}$, of one or more reference dispersions each having known total particle surface area per unit volume of liquid, $A^{ref}_T$;

ii) computing the proportionality constant, $k_{AL}$, for the reference dispersion from the equation, $R_n^{ave,ref} = k_{AL}^{ref} A_T^{ref}$; where n=1 or 2;

iii) determining an average NMR relaxation rate constant $R^{ave,sample}$ or $R_2^{ave, sample}$ of a sample dispersion whose surface area is to be determined; and iv) computing the total surface area of the sample dispersion, $A_T^{sample}$ from the equation, $R_n^{ave, sample} = k_{AL}^{ref} A_T^{sample}$, where n=1 or 2, wherein the variables used herein are defined in the detailed discussion.

A further embodiment of the invention is a compact and portable device for the analysis of dispersions by low-field pulsed NMR that provides a user with a series of predetermined actions or steps through either hard-wired of software algorithms for the measurement of one or more characteristics of the phases or particles comprising the dispersion selected from the group consisting of surface area, solid/liquid ratio, particle size, surfactant adsorption, and elemental analysis.

These and other embodiments are described in the following detailed description of the invention which should be read in conjunction with the accompanying drawings.

DETAILED DESCRIPTION OF THE INVENTION

For the purposes of the description of the current invention the terms device, instrument and spectrometer are used interchangeably.

For the avoidance of doubt the word "comprising" is intended to mean "including" but not necessarily "consisting of" or "composed of." In other words, the listed steps or options need not be exhaustive.

Except in the operating examples, or where otherwise explicitly indicated, all numbers in this description indicating physical, electrical, magnet, or dimensional parameters are to be understood as modified by the word "about."

Components of Portable Device

The first embodiment of the invention is a portable and compact device for the measurement of the in-situ surface area, particle size, or other physical properties of dispersions by low-field pulsed NMR.

By physical properties are meant a collection parameters that characterize the microscopic state of the dispersion either of the particles, their interfaces or the phase themselves and that generally control the overall properties of the dispersion, e.g., its stability or viscosity. These include but are not limited to: particle or droplet size, surface area (total and specific), diffusion coefficients, solid/liquid fraction, elemental makeup, adsorbed species and wettability.

The term portable primarily relates to the weight of the device. To be portable in the current context the total weight of all its component modules (excluding any external computer) should be no more than about 20 kg, preferably less than 10 kg, more preferably less than about 5 kg, and still more preferably less than about 3 kg.

The term compact refers to both the "total footprint area", i.e., the total area occupied by the collection of individual component modules comprising the device, and its overall maximum elevation, i.e., the overall height of the device measured from its bottom to its highest point but without subsidiary components such as the sample container. In the context of the current invention, the term compact is defined as an instrument wherein the total foot print area occupied by all the modules making up the instrument is no greater than about 0.30 m$^2$, preferably less than about 0.25 m$^2$, more preferably less than 0.2 m$^2$ and most preferably less than about 0.1 m$^2$ and wherein the maximum elevation of the device is no greater than about 0.45 m, preferably less than about 0.3 m (about one foot), and more preferably less than about 0.2 m. Ideally, all the components of the device (which does not include an external computer) should fit in a small cabinet typically the size of a shoe box.

One of the key operating properties of the instant NMR device which allows it to be truly compact and portable is its low operational power demands (steady state power consumption). This has been achieved by selection and optimization of the various components based on extensive research. The device should have power consumption of less than 500 W, preferably less than 200 W, more preferably less than 150 W, and still more preferably around 100 W to 150 W.

It has been found through experimentation and theoretical analysis that for most of the measurements required to extract the physical properties of dispersions addressed herein do not require the highly uniform magnetic fields characteristic of a large high field instrument. The field magnet is required to produce an NMR free induction decay of greater than 20 microseconds but preferably greater than 50 microseconds. In this case it has been found possible to streamline the electronics and design the circuitry to use less power.

Advantages of very low power consumption are: i) the instrument can be mobile and even operate on batteries; ii) temperature fluctuations from heating are reduced leading to greatly improved stability, especially of the magnet; iii) lower power translates to less weight because of less need for cooling fans, heat sinks; and finally iv) low power consumption ultimately allows a smaller overall footprint and weight because of smaller power supplies and smaller components.

The power required by the device can be provided by ordinary external AC current, by an optional DC disposable or rechargeable battery (for enhanced portability), or by a combination of these modes.

By in-situ surface area is meant the surface area of the dispersed phase (i.e., particles) that is actually exposed to and in contact with the continuous phase, e.g., liquid phase, of the dispersion. Thus, the current device measures surface area in the dispersion as opposed to measurement of the surface area of a dry powder via gas adsorption, e.g., the BET method.

The theory of pulsed-gradient NMR measurements is well established since the seminal work by Tanner and Stejskal (J. Phys, Vol 42, P288 (1965)). In addition to the references cited above many treatises are available including: "Pulse and Fourier Transform NMR", T. C. Farrar and E. D. Becker, Academic Press, New York (1971) and P. T. Callaghan *Principles of Magnetic Resonance* OUP (1991), M. Levitt *Spin Dynamics* J. Wiley (2001).

Many nuclei, for example, that of the hydrogen atom, have a net magnetic moment. In the presence of an applied magnetic field $B_0$ (z) and at thermal equilibrium a net magnetization, $M_z$ arises along the field direction (z). The value of this magnetization depends on the strength of the magnetic field which separates the nuclear spin energy levels. If a suitable radio frequency (RF) pulse is applied to the sample at a frequency that is in resonance with the energy level separation, $M_z$ can be tipped through any arbitrary angle with respect to z. When the RF field is removed the magnetic moments return to their net equilibrium orientation along z. During this process, which is called relaxation, a small signal can be detected in a coil wrapped around the sample. The nuclear relaxation times measured correctly depend on molecular mobility and can be used to identify different states of matter including solids, liquids and molecules adsorbed at interfaces. The addition of a magnetic field gradient enable spins in different physical locations to be identified and this is the basis on magnetic resonance imaging.

Using a suitable combination of RF pulses and data analyses, two relaxation times, $T_1$ (spin-lattice) and $T_2$ (spin-spin) can be obtained.

As will be discussed below, different sequences and combinations of RF and magnetic field pulses are required to optimally measure different properties of a dispersion. Consequently, in order to be most versatile as a dispersion analyzer, i.e., to allow the most information to be extracted from the sample, the instant device should be capable of providing a variety of RF and magnetic field gradient pulse combinations and sequences and be capable of accurately extracting the relaxation times from the emitted signals.

Figure 1:
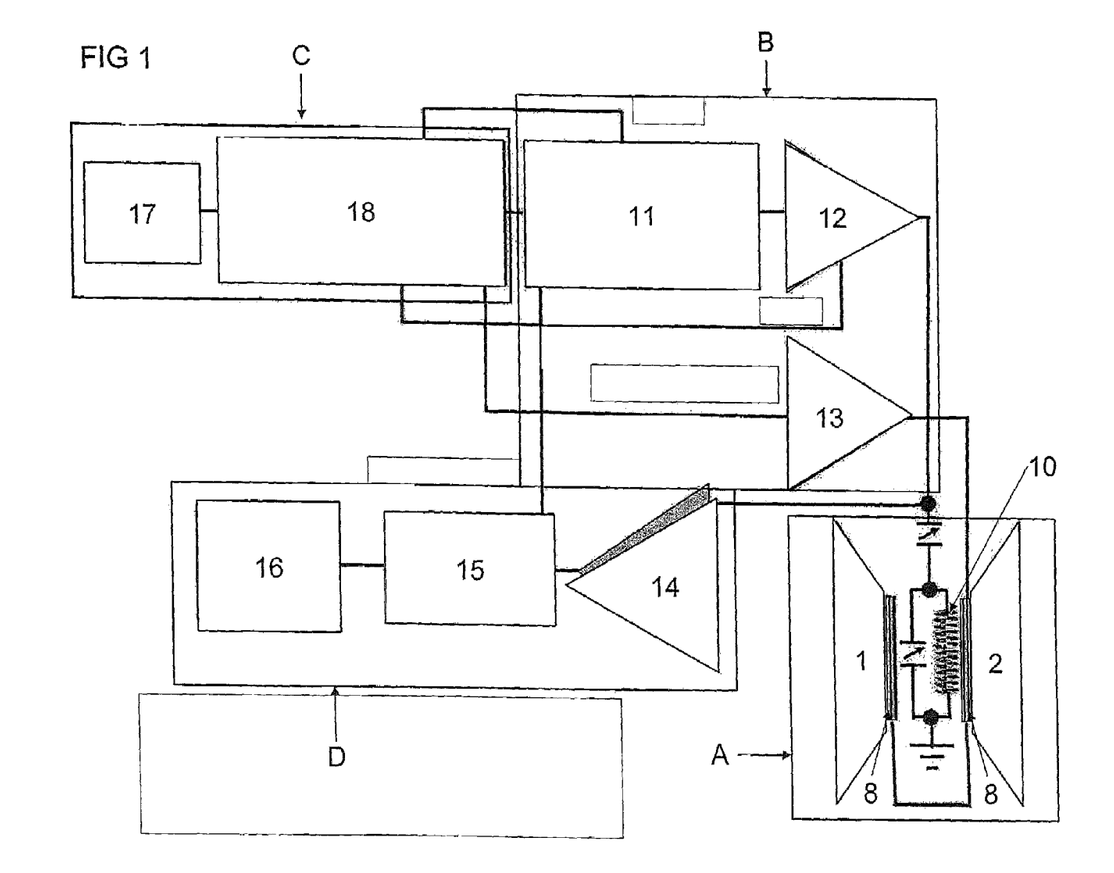
FIG. 1 is a schematic view of the NMR device showing the key modules.

The key components by which this is accomplished within the constraints of portability and compactness are described below and conveniently grouped into four modules. With reference to FIG. 1 these modules include: an NMR probe module A, pulse generator B, signal processor C and master controller D. However, it is important to note that this description is a convenient way to group the functions performed by the various components that make up the device. These components however need not be spatially segregated into discrete areas as depicted in FIG. 1 in the instrument rather only that the components be present that collectively perform the functions of each module with the required tolerances.

The modules discussed below can be placed in one or more cabinets by which we mean that they can be physically separated and connected through cables or even by wireless transmitting means.

However, in a preferred embodiment, all the modules are housed within a single cabinet having a total footprint area less than about 0.25 m², an elevation less than about 0.45 m, a weight less than 20 kg, and an operating power demand less than 200 W.

The key modules are described below.

NMR Probe Module A

With reference to FIG. 1, the probe module A comprises a pair of opposing field magnets 1 and 2 that define a chamber 3 which should be of a sufficient size to accommodate the transmission and detection means (see below) and the experimental sample holder which is a generally a glass tube of the type used in NMR spectroscopy. The distance between the magnet faces is of the order of 2 cm and the chamber has a volume of about 1 cm³.

The magnets 1, 2 are preferably permanent magnets such as those comprised of samarium cobalt or neodymium iron boron alloys. In principle, electromagnets can be employed provided they are sufficiently light, compact and do not have excessive power requirements. The field magnets should provide a magnetic field strength of at least about 0.2 Tesla (2 kG), preferably 0.3 Tesla, and more preferably at least 0.4 Tesla. The required field uniformity depends to some extent on the type of dispersion information required but should have a variation over a sample volume of 1.0 cm³ of less than about 1 part in $10^3$, preferably 1 part in $10^4$ and more preferably 1 part in $10^5$.

Figure 2A:
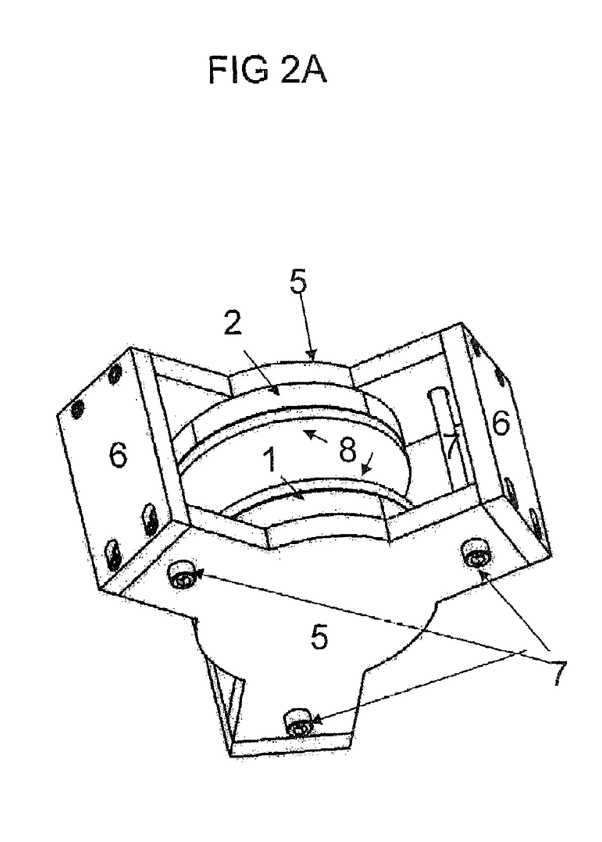
FIG. 2A is perspective view of the magnet and yoke assembly.
Figure 2B:
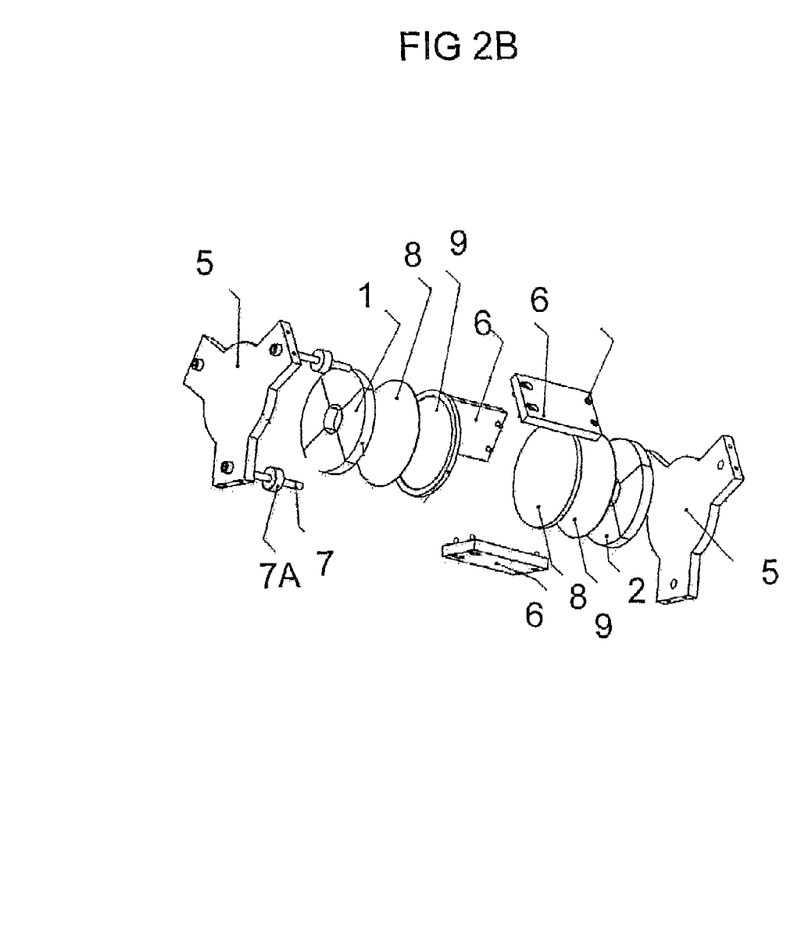
FIG. 2B is a side exploded view of the magnet and yoke assembly.

With reference to FIG. 2A and FIG. 2B, which provide an exemplary design, the field magnets 1, 2 are held in place by a yoke 4. Yokes can be of various designs and constructed of various materials provided they are light weight and provide adequately low magnetic reluctance so that field uniformity is not compromised. In one embodiment, the yoke assembly has 3-fold symmetry and is comprised of three arms or members fitted with adjustable alignment screws. As shown in FIG. 2A and FIG. 2B, the yoke may comprises two end members 5 adjustably joined by three lateral joiners 7. In the exemplary design, the three aligning screws 7 (typically mild steel) and collars 7A provide a convenient way to align the faces of the field magnets 1, 2 to achieve maximum uniformity. It should be recognized that the aligning screws could also be adjustably coupled to a servo mechanism so that alignment can be carried out remotely and even be computer controlled although this is less preferred because of added complexity, weight and cost.

Pole pieces (pole caps) 9 comprised of a suitable material are optionally employed to enhance field uniformity and in the exemplary design are separated from the inner faces of the magnets (faces that are directed towards the chamber) by shims 8.

The probe module A further comprises means located within the chamber 3 for transmitting both radio frequency pulses, detecting magnetic responses (signals from the sample) and delivering magnetic field gradient pulses. In an exemplary design this is accomplished by a single coil 10 located within the chamber such as single coil comprised of 80 turns of insulated copper wire wound around a PTFE former, the latter having an axial hole of suitable dimensions to allow the insertion of a standard NMR sample tube. The detection means should be sensitive over a length of about 5 mm. The NMR line shape can be used to estimate the homogeneity over the sample volume.

The probe module A should be as light and compact as possible and should not exceed 20 kg, preferably be less than 10 kg and most preferably less than 5 kg.

Pulse Generator B

The pulse generator B has two functions. Firstly, it provides a selectable means for generating radio frequency pulses of typically about 10 W up to about 200 W at frequencies between about 1 and 30 MHz over a duration of about 1 to about 50 μs.

Secondly, the pulse generator needs to provide a magnetic field pulse that generates a magnetic field gradient across the sample volume (1.0 cm³) of up to 1 $Tm^{-1}$ to overcome the inherent magnetic field inhomogeneity, especially for diffusion based measurements.

With reference to FIG. 1, the pulse generator B comprises a digital RF frequency source 11 selectable to about 1-30 MHz, and a power amplifier 12. In a preferred embodiment RF pulses of up to 200 W are provided by an amplifier which is powered by the discharge of one or more capacitors. The coil 10 and associated capacitors are parts of a resonant circuit. These capacitors are tuned and matched to the probe module A. These components can be voltage controlled capacitors (varactors) but more simply can be manually tuned variable capacitors.

The pulse generator B further includes a magnetic field gradient driver 13 that produces a selectable current of from about 0.2 up to about 20 amps into the gradient field coil of series resistance between about 0.5 and 2Ω load in order to generate the magnetic field gradients required (up to about 1 $Tm^{-1}$). Again, the discharging of one or more capacitors provides a compact and low power demand option to achieve the required currents.

The pulse generator B includes a software controlled RF oscillator with gating to provide pulses of variable amplitude, phase and length and an RF power amplifier to transmit pulses to probe coil. For RF pulse generation turn-on and turn-off times are less than 1 microsecond. The period of each pulse is from 1 microsecond to 2 milliseconds.

For magnet pulse generation, the software controlled pulse generator provides pulses of variable magnitude and timing to the field gradient coil. Turn-on and turn-off times are less than 10 microseconds. Periods from 100 microseconds to 10 milliseconds, currents up to 20 amps and control to +/-2% are preferred.

Signal Processor C

The signal processor C provides the means for detecting, amplifying, filtering, digitizing and storing signals acquired from the probe module A.

The NMR signal from the probe module A is of the order of a few μV and requires a very low noise pre-amp 13 providing about a 30 dB gain. This signal undergoes further amplification (60 dbs) followed by digital phase detection and an A/D converter or similar converter to give a measurable signal. This is preferably provided by digital filters and an A/D converter 15. The signal is then signal averaged by a signal processing unit 16 before being transferred to a main central processor unit for further data reduction and display.

After amplification, the ADC output is typically filtered to a band width of 1 mHz The interim data collected can be viewed as text, for example on an optional small LCD display. In a preferred embodiment, data is stored on a memory card within the unit and subsequently transferred to a conventional micro computer such as an ordinary laptop computer through a conventional interface, e.g., USB cable. For example, data storage by FIFO static ram configured a 64K×16 is suitable.

The data acquisition needs to be at least 10 bits resolution and a data rate maximum of 10 MHz (variable). Typically the storage of about 500 data points is required.

Master Controller D

The master controller D performs the function of timing, gating, and sequencing the radio frequency pulses and magnetic field gradient pulses and controlling their respective frequencies, phases, and field gradients.

A clock 17 provides the basic timing while the gating and pulsing circuitry 18 provides the means for controlling pulse gating, timing, sequencing, and frequency selection for both the RF pulses and pulse gating, timing, and sequencing for the magnetic field gradient pulses and is best carried out utilizing a programmable sequence generator. A controller based on a Xilinx FPGA using VHDL language is suitable.

At least three different pulse outputs are required and these need to be programmable from a main cpu. These outputs are: a first output to gate the RF, a second output to drive the field gradient pulses (variable length and amplitude) and a third output to switch the RF phase.

The timing requirements are significant. For example, rise and fall times of the pulses are less than 0.1 μs and the pulse lengths (duration) are programmable to an accuracy of 0.5 μs with lengths from 0.5 μs to 10 ms. Preferably all timing should be better than +/−0.1 μs. The pulsing cycle needs to be repeated every 1-10 s for a preset number of signal averages. Sequencing pulses have a step size of less than 0.1 μs with 0, 90, 180, and 270 degree phases. Once the acquired signal is transferred to the host processor and suitably reduced, the sequence is restarted with different parameters depending on the experiment being performed, i.e. the type of measurement being made. For example, for diffusion, the gradient field amplitude should be incremented. Once the chosen number of experiments has been performed all the data can be reduced to give the required parameters, e.g. the diffusion coefficient. Some typical pulse sequences are discussed below.

Pulse Sequences, Data Acquisition and Processing

Pulse sequences: Several pulse sequences must be programmed including single pulse and those required to measure $T_1$, $T_2$, and to perform 1D imaging and diffusion. Some other simple sequences are also be useful for calibration of unknown samples. All sequences are programmable through a simple pulse programming language and through an optional visual display.

Data acquisition and processing: The signal following the pulse excitation are digitized and stored and averaged in hardware. In some cases a magnitude spectrum will suffice so both the real and imaginary parts could be combined and summed as $$I(Q, t) = \sum_{i=1}^{n} [\sin^2 I_i(t) + \cos^2 R_i(t)] \quad (1)$$

where $I_i$ (t) is the intensity of the imaginary (90 degrees out of phase) component of the ith data point and $I_r$ (t) is the real (in phase) component of the same and I (Q, t) is the resultant magnitude spectrum after adding n spectra.

For the simple sequences, data collection can start immediately after the pulse (1-2 μs) delay and end after 1-5 ms. If there is a DC offset, this needs to be measured by making a separate data acquisition either before the initial sequence or after the signal has reached the baseline (20 ms). Phase cycling for coherent noise reduction can be implemented. For the spin-echo sequences (see below) the data acquisition can start after the 180° pulse and continue for approximately 4 ms. These times will vary for different samples, but these are reasonable starting estimates. The measurement of $T_2$ requires multiple 180° pulses with a 90° phase shift between the initial 90° and the 180°. Signal acquisition begins after the first 90° pulse and can be restricted to the echo maxima.

Experimental Procedures

There are several basic set-up procedures depending on the sample to be measured and what information is required. The following examples are illustrative and are in no way to be interpreted as limiting the scope of the invention. Three basic experiments are illustrated: solid/liquid ratio, solid dispersion surface area and emulsion droplet size via diffusion measurements. These are also discussed below.

Set-Up

In order for the spectrometer to operate properly a number of set-up sequences must be run. The first task is to find a signal bearing in mind that the temperature of the magnet will affect the field and hence frequency. Nominally a frequency between 9 and 15 MHz is employed but initially a low field is useful. If 10 MHz is chosen, then the frequency in Hz ν is given by $$\nu = \frac{\gamma B}{2\pi}$$

where γ is the gyromagnetic ratio and is equal to 26.752× 107 rad $T^{-1}s^{-1}$. For 10 MHz this gives a field of 0.23 T.

(a) Adjust frequency for resonance. A single RF pulse and immediate data capture is required. This can be done by adjusting the frequency of the oscillator manually with padding or digitally by changing the synthesizer. The display will show a modulated decay. Aliasing may occur if the frequency is higher than half the ADC sampling rate. If the frequency is outside the bandwidth of the system there will be little or no response. The software automatically scans and steps the frequency.

(b) Adjust tuning/matching for maximum signal. This adjustment also depends on frequency and can be carried out manually by adjusting the probe capacitors or by software control.

(c) Adjust pulse length for 90° pulse. When the first two adjustments have been made then the pulse length should be set for a maximum signal.

(d) Adjust pulse length for 180° pulse. Similarly when the first two adjustments have been made then the pulse length should be set for a minimum signal.

Verification Tests

To check the spectrometer is functioning properly the following sealed standard samples should be run.

(a) Sensitivity test. Use standard sample 10% $H_2O$ in $D_2O$. This should give a signal to noise ratio of approximately 10:1 or better.

(b) Resolution test line width. If the environment is free from external magnetic fields then the frequency resolution should be approximately 10 kHz.

(c) Relaxation test $T_1$. This is a test that the pulses are set properly. Choose a repeat time of about 1 s. The display will give 10 points on the relaxation decay with Δ spacings from 0.1 to 50 ms. Typical values for $T_1$ for water containing 0.1M $CuSO_4$ $T_1$ is approximately 10 ms.

(d) Diffusion Test. This is the most exhaustive test. The gradient amplitude is varied between 0 and 100% and the final integrated data should fit a gaussian function (Equation 4). For $D_2O$ doped water a Diffusion coefficient value of approx 2.4×$10^{-9}$ $m^2$ $s^{-1}$ at ambient temperature should be found.

Application Sequences

The following are illustrative examples of possible applications of the low-field pulsed NMR dispersion analyzer and the types of pulse sequencing and data analysis required.

Figure 3:
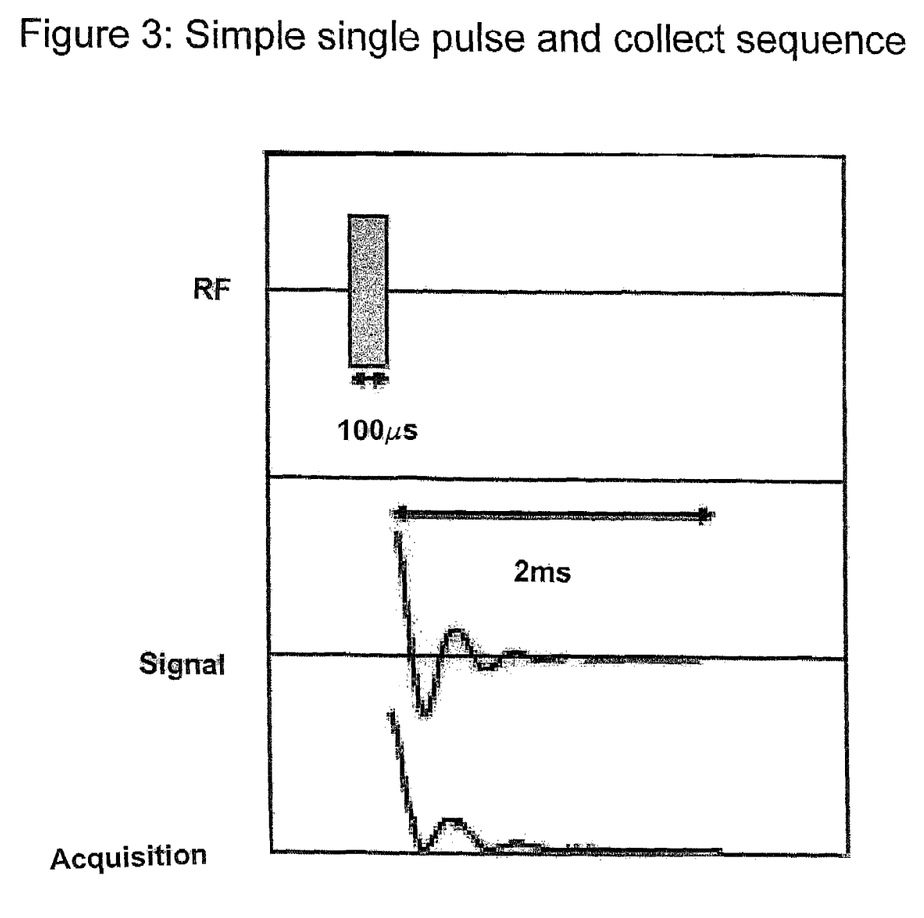
FIG. 3 illustrates a simple single pulse and collect pulse sequence.
Figure 4:
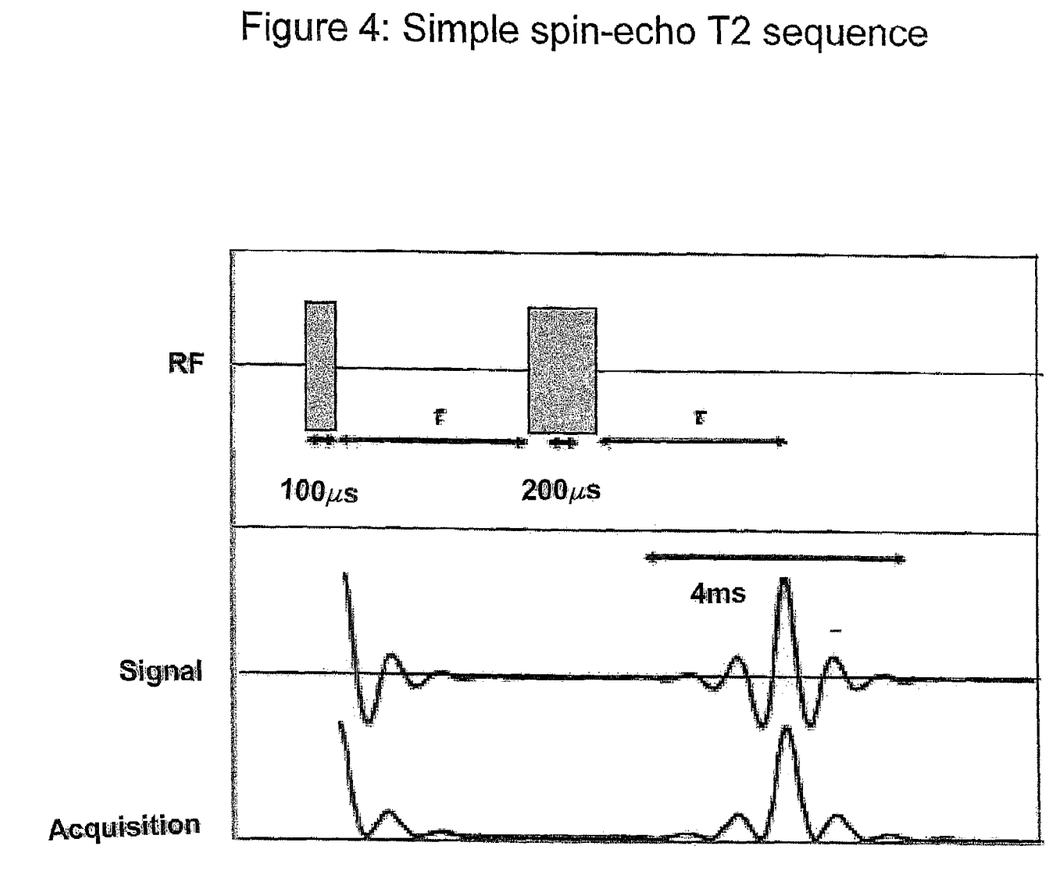
FIG. 4 illustrates a simple spin echo pulse sequence.

(a) Solid/liquid ratio. In the solid liquid ratio measurement a pure liquid is required for calibration of the spectrometer. For a full scale reading, the appropriate pure liquid is run with a single pulse experiment (see FIG. 3) for a preset number of accumulations using a long repetition time. The unknown sample is run for the same length of time and the relative intensities of the two data sets are recorded. An alternative is to use the spin-echo experiment mode (see FIG. 4) which will compensate for field homogeneity. The sensitivity of the method will depend on the number of accumulations required. Typically 1-10% would be reasonable to achieve.

(b) Surface area measurements. NMR relaxation times can be used to measure total surface area for a dispersion of particles in a fluid. The basic idea is that a molecule adsorbed at an interface has a much shorter relaxation time than one in the bulk. Typically for silica dispersed in water the bulk $T_2$ will be of the order of 2 s, whereas the surface $T_2$ will be of order 1 ms. In the fast exchange limit we measure a dynamic average of these times. If we define the relaxation rate constant $\bar{R}_2$ as the reciprocal of $T_2$. The average rate constant $\bar{R}_2$.

$$\bar{R}_2 = p_b R_{2b} + p_f R_{2f} \quad (2)$$

where f and b refer to bound and free, respectively and $p_f$ and $p_b$ refer to the fractions of free and bound water, respectively.

In order to refer these values directly to surface area it is useful to define a specific relaxation rate $R_{2sp}$ which is defined as $$\bar{R}_{2sp} = \frac{\bar{R}_2 - R_{2water}}{R_{2water}} \quad (3)$$

Figure 5:
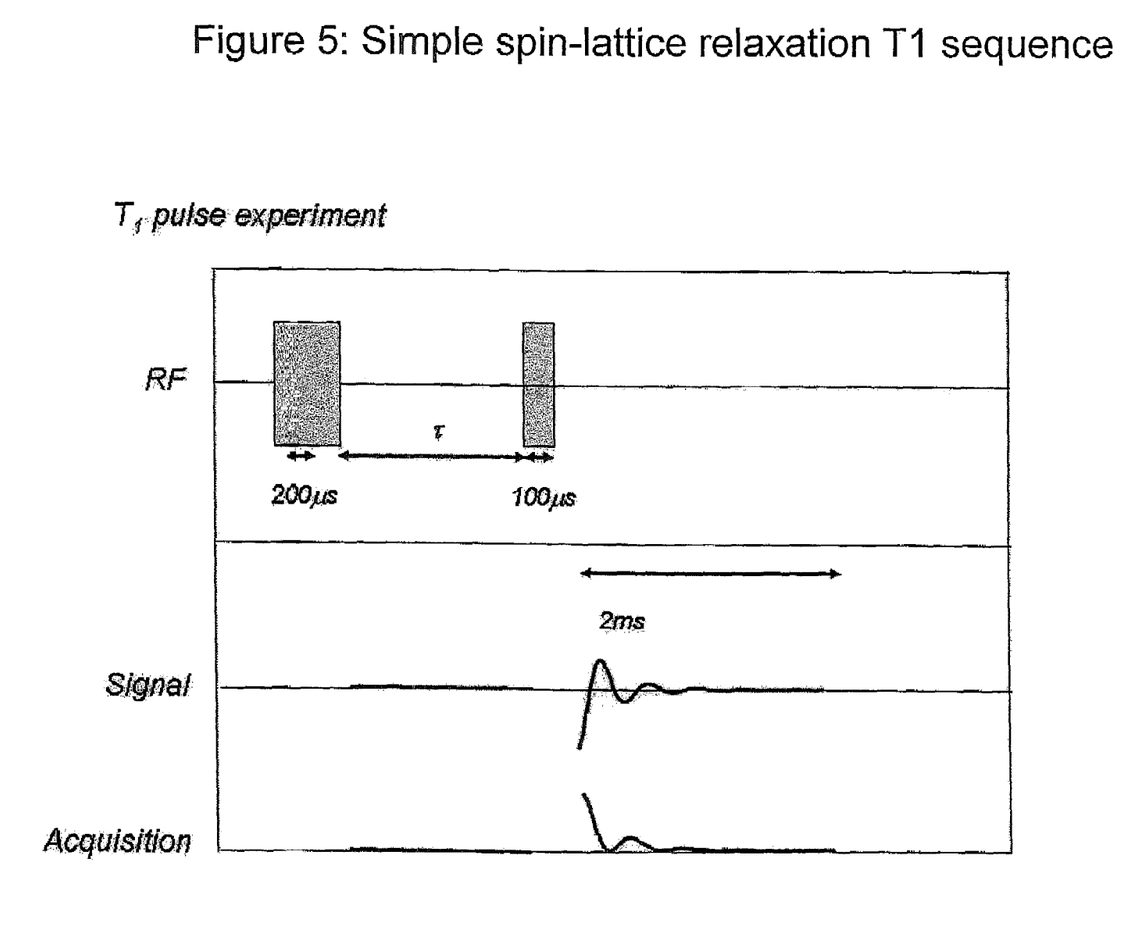
FIG. 5 illustrates a simple spin-lattice relaxation $T_1$ pulse sequence.
Figure 6:
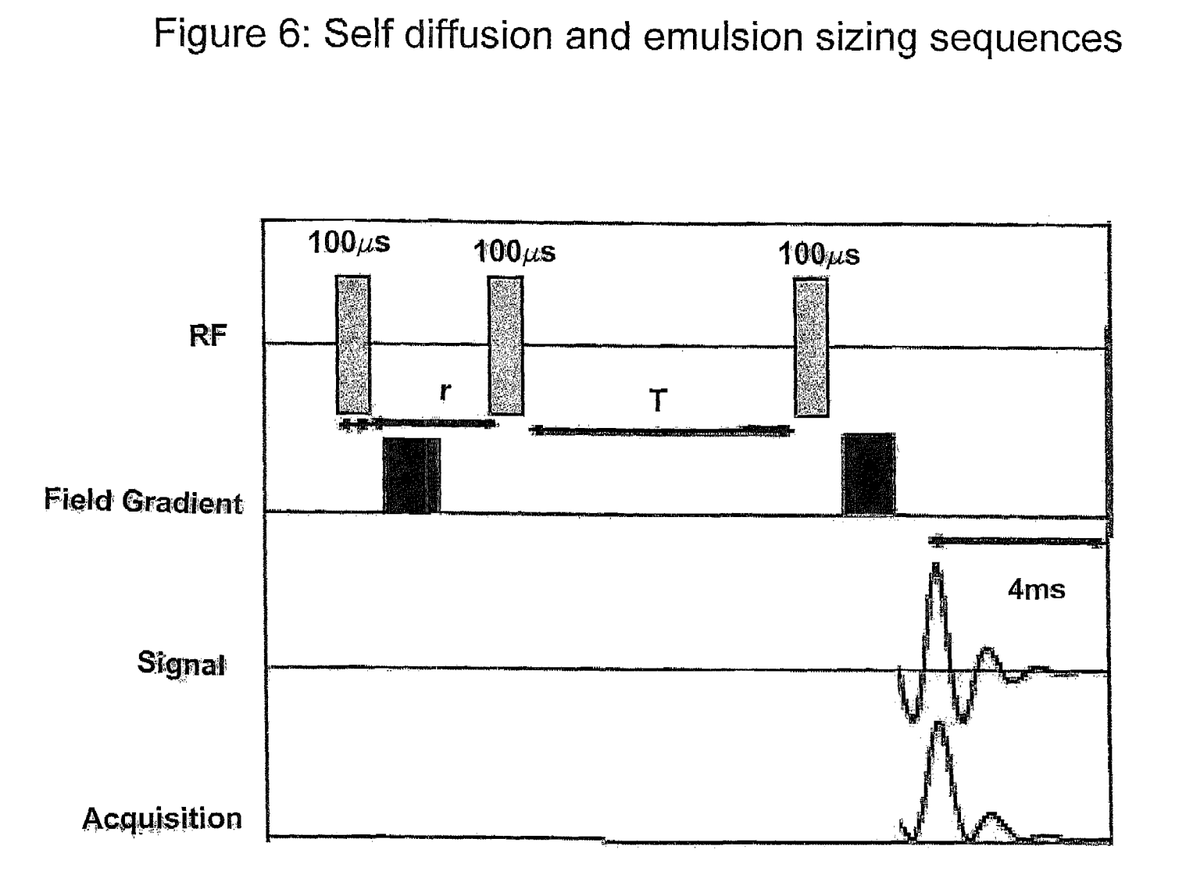
FIG. 6 illustrates emulsion sizing pulse sequence.

By calibrating with a known sample then $R_{2sp}$ is proportional to the total surface area in the sample. The experiments can use either a $T_2$ (see FIG. 5) or a $T_1$ (see FIG. 6) pulse sequence. Typically 10 data points would suffice at each $\tau$ value. The range of values depends on the standard sample but would be typically between 0.1 and 100 ms. Example 1 below illustrates the method in more detail.

c) Diffusion measurements. These experiments can determine not only the values of the self-diffusion coefficient of the system but also for certain systems (emulsions) particle size estimation. The pulse sequence is shown in FIG. 6. The experiment requires sampling as much of the spin-echo signal as possible. Typically, the field gradient intensity is increased in 10 steps up to the maximum gradient depending on the sample being measured. For bulk water with unrestricted diffusion typical parameters would be $\tau=20$ ms, $\delta=1.0$ ms and gradient 0.01 to 1.0 Tm−1. These parameters would give a decay curve which follows the function.

$$\frac{I(G)}{I(0)} = \exp(-\gamma^2 G^2 \delta^2 (\Delta - \delta/3) D) \quad (4)$$

The range of diffusion coefficients that can be measured will depend on several factors including the field stability, sensitivity (signal to noise) and the relaxation times. Water has a diffusion coefficient D of $2.4 \times 10^{-9}$ m$^2$ s$^{-1}$ and the lower limit of measurement will be on the order of $10^{-13}$ m$^2$s$^{-1}$. Liquid droplet sizing utilizes the fact that the dispersed phase cannot diffuse distances greater than the droplet size. Under these conditions if the diffusion time $\Delta > l^2/2D$ then the attenuation function in Equation 4 becomes $$\ln\left(\frac{I(G)}{I(0)}\right) = \frac{54 G^2 a^4 \gamma^2 \left(3\left(e^{\frac{13D(\Delta-\delta)}{3a^2}} - e^{\frac{13D\delta}{3a^2}} - e^{\frac{13D\Delta}{3a^2}} + e^{\frac{13D(\Delta+\delta)}{3a^2}} + 2\right)a^2 - 26D\delta\right)}{15379 D^2} \quad (5)$$

This enables a value of the droplet interior radius a to be determined. Under certain conditions it is expected that an approximate polydispersity index can be obtained but this will depend critically on the signal/noise and other sources of systematic error.

(d) Elemental analysis/liquid state. This is another use of the simple sequence given in FIG. 3. In this instance the spectrometer is tuned to the appropriate frequencies as shown in Table 1. Atomic concentrations of the listed elements can be determined from the measured initial signal intensity of the unknown sample to that of standard concentration samples of the respective elements.

TABLE 1

NMR Frequencies at 0.694 T

| Nucleus | Frequency/MHz |
|---|---|
| $^1$H | 30.0000 |
| $^{19}$F | 28.2231 |
| $^{31}$P | 12.1443 |
| $^7$Li | 6.2763 |

EXAMPLE 1

This example illustrates the use of low-field pulsed NMR to measure the surface area of the dispersed phase in a dispersion.

Figure 7:
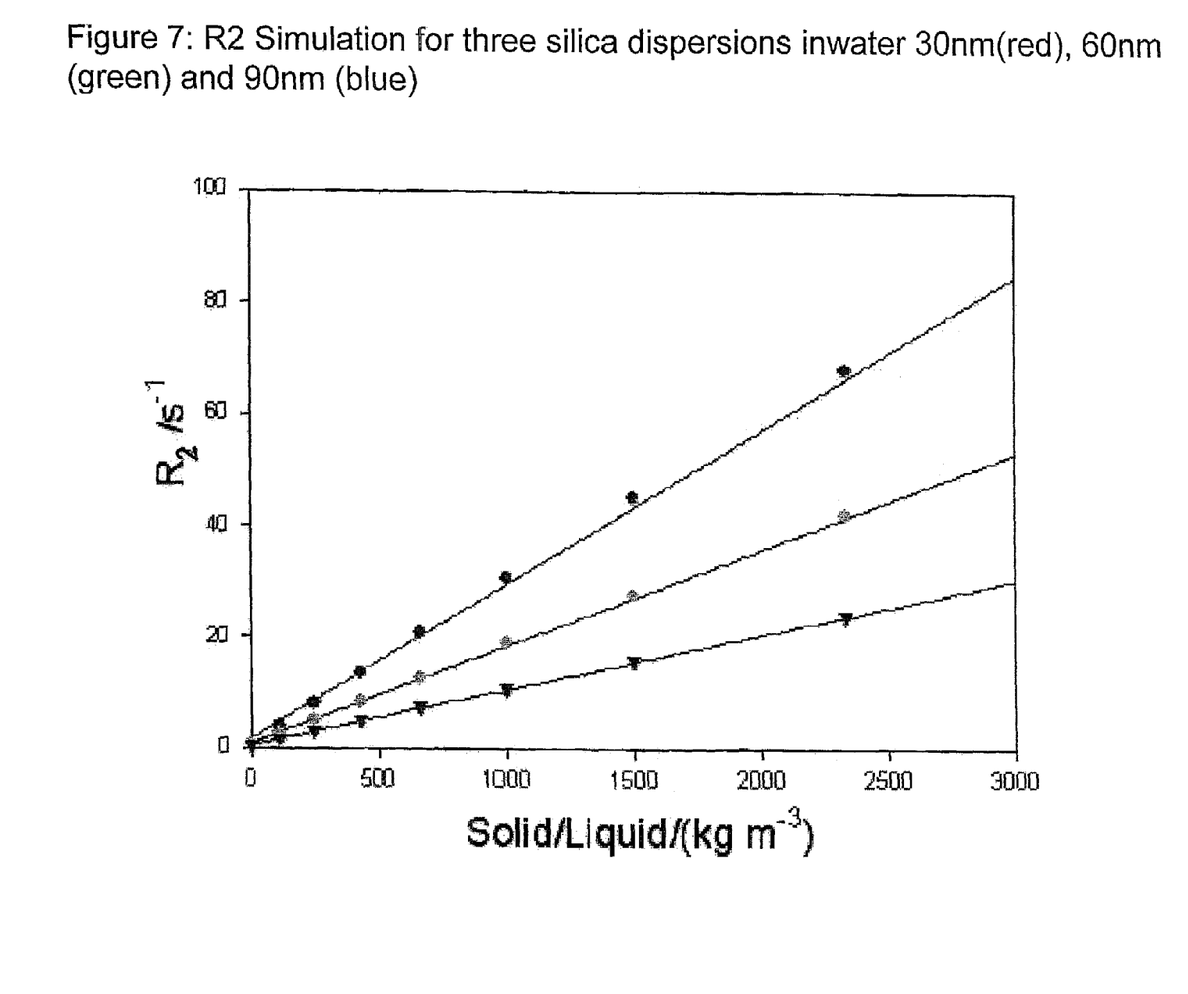
FIG. 7 is an example of a $R_2$ simulation for three silica dispersions in water: 30 nm, 60 and 90 nm particle sizes.

FIG. 7 shows a simulation for a range of silica dispersions with different sizes showing that the slope is dependent on particle size if the data is plotted as a function of the solid/liquid ratio. This ratio is given by Equation 6A $$\bar{R}_n = k_{SL} \frac{\text{Solid}}{\text{Liquid}} = k_{SL} \frac{\phi \rho}{1 - \phi} \quad (6A)$$

where $\Phi$ is the volume fraction of particles and $\rho$ is the particle density and $k_{SL}$ is a constant.

Figure 8:
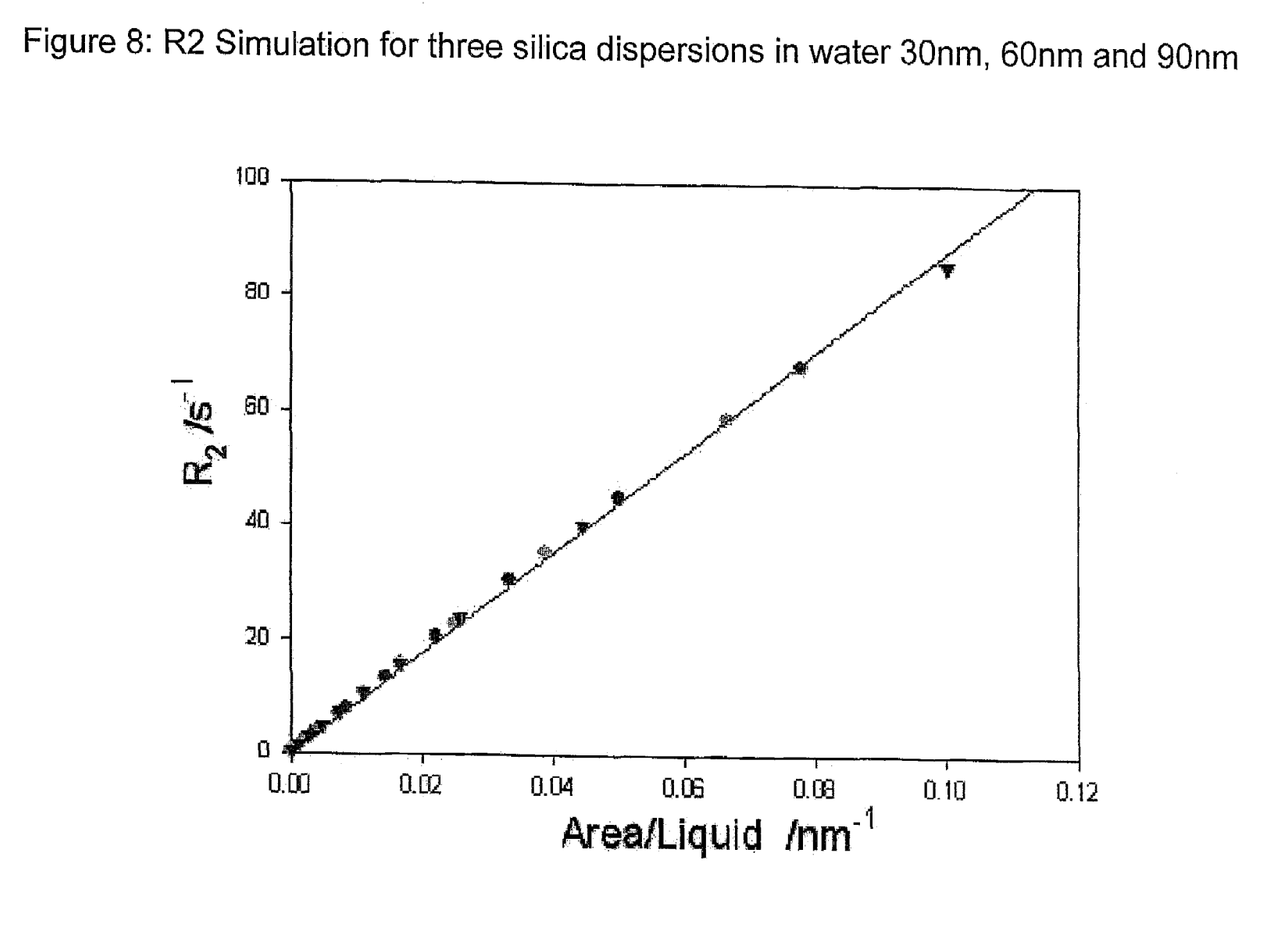
FIG. 8 is an example of $R_2$ simulation using results from FIG. 7 as a function of Area/Liquid ratio.

If the surface area is known then the data can be plotted as a function of the surface area/liquid ratio and then all the data collapse onto a single straight line as shown in FIG. 8. This ratio is given by Equation 6B.

$$\bar{R}_n = k_{AL} \frac{\text{Area}}{\text{Liquid}} = k_{AL} \frac{A_S \phi}{\rho (1 - \phi)} \quad (6B)$$

where $A_S$ is the surface area of the particle. In the case of a spherical particle this could be written as simply 3 $\rho$/r where r is the particle radius. The two constants (k) are related by:

$$k_{AL} = k_{SL}\frac{\rho^2}{A_S} \quad (7)$$

The slopes taken from FIG. 7 are themselves linear with surface area, so that if the surface area or particle size (if spherical) of one sample is known then the surface area or particle size of an unknown sample of the same type can be found. For example, with a sample of known specific surface area, $A_S$, $k_{AL}$ can be found from a graph of Equation 6A or 6B and then the same equation can be used for an unknown sample. It is also useful to normalize effects of the solvent by defining a specific relaxation rate constant $R_{n,sp}$ which is defined here for a dispersion in water as $$\overline{R}_{n,sp} = \frac{\overline{R}_n - R_{n,water}}{R_{n,water}} \quad (8)$$

Figure 9:
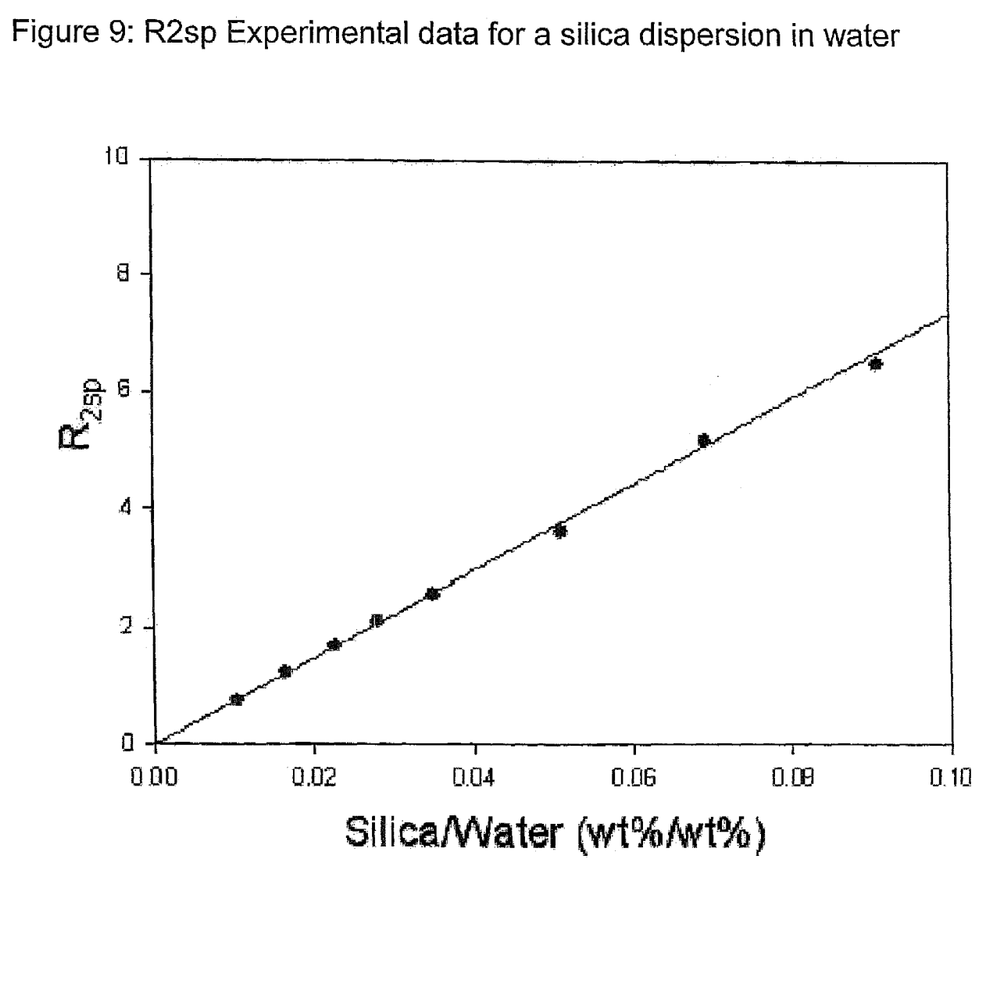
FIG. 9 is a graph of experimental results of measurement of $R_{2sp}$ for a silica dispersion in water.
Figure 11:
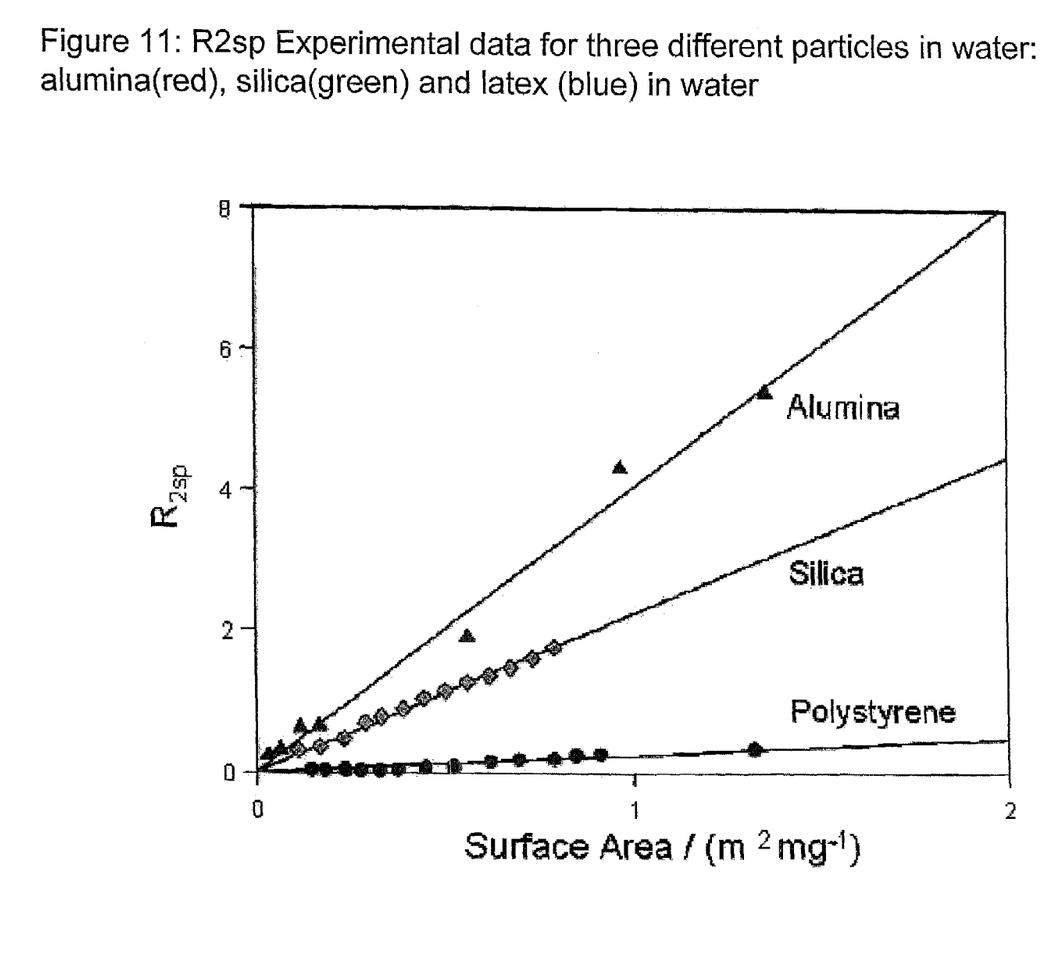
FIG. 11 is a graph of $R_{2sp}$ experimental data for three different particles in water: alumina (triangles), silica (diamonds), and polystyrene latex (circles).

Some typical experimental data for $R_{2sp}$ for a silica dispersion in water are shown in FIG. 9. The factor $k_{AL}$ in Equation 6B is also a useful parameter as it depends on the wettablility of the dispersed phase and the atomic composition. FIG. 11 shows a series of data for three different substrates, alumina, silica and a polymer latex. Clearly, the latex is much more hydrophobic than either of the oxide surfaces.

The experiments can use either a $T_2$ (see FIG. 4) or a $T_1$ (see FIG. 5) pulse sequence. Typically 10 data points would suffice, i.e., 10 values of $\tau$. The range of values depends on the standard sample but would be typically between 0.1 and 500 ms for $T_1$. For $T_2$ the situation is slightly more complex as multiple pulses are required. It is also necessary to accumulate the signal at each $\tau$ value. In order to calculate the surface area per gram the solids concentration of the sample is also needed and this can be obtained from the signal intensity compared to the pure solvent.

EXAMPLE 2

Figure 10:
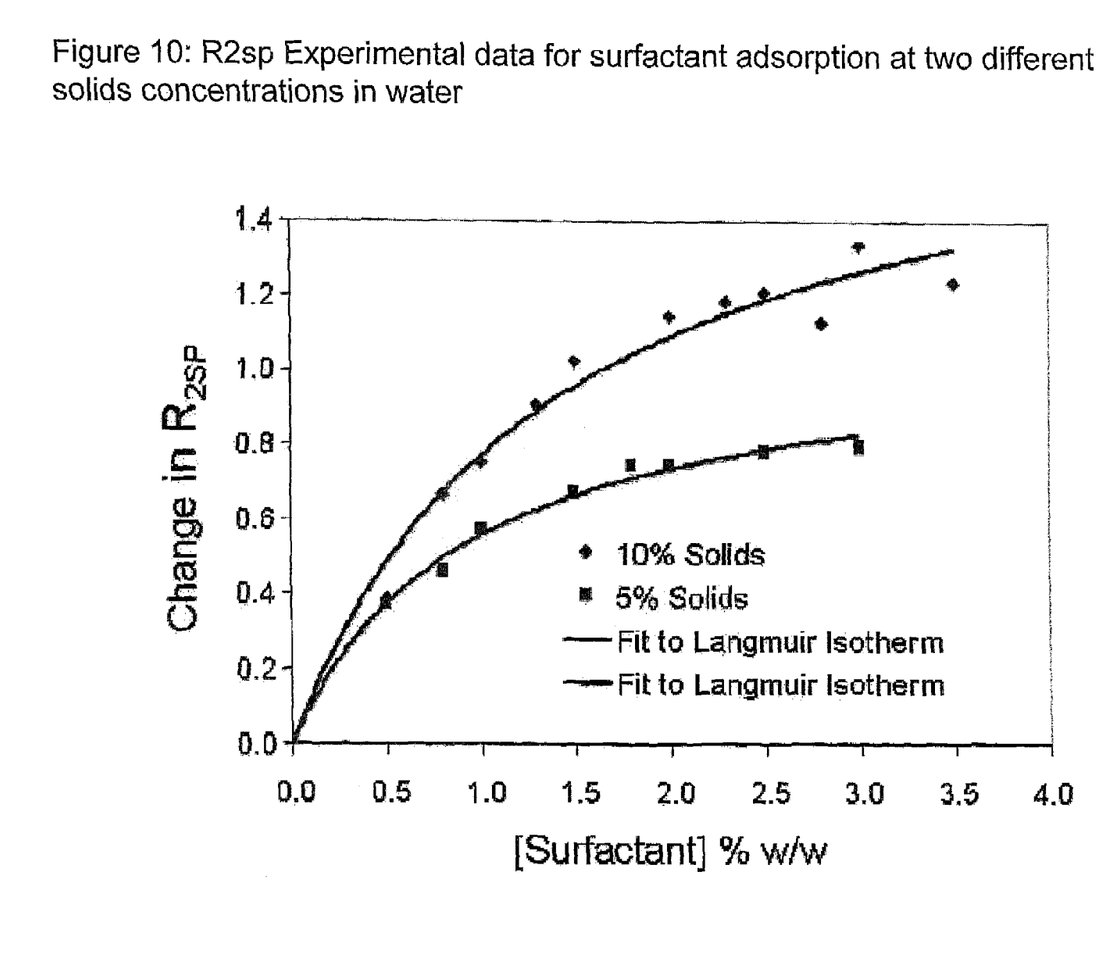
FIG. 10 is a graph of $R_{2sp}$ experimental data for surfactant adsorption at two different solids concentrations in water.

This example illustrates another application of the instant invention in measuring dispersion properties, namely the measurement of an in-situ adsorption isotherm. This works because of the effect of an adsorbent on the bound water layer. Data at two different solids concentrations are shown in FIG. 10 with the solid lines being a fit to the Langmuir adsorption isotherm.

While this invention has been described with respect to particular embodiments thereof, it is apparent that other forms and modifications of the invention will be obvious to those skilled in the art. The appended claims and this invention generally should be construed to cover all such obvious forms and modifications which are within the true spirit and scope of the present invention.

What is claimed is:

1. A compact and portable device for the analysis of dispersions by low-field pulsed NMR comprising: an NMR probe module, a means for generating radio frequency and magnetic field gradient pulses, a signal processor, and a master controller; wherein said compatible and portable device measures one or more characteristics of the phases or particles comprising the dispersion selected from the group consisting of surface area, solid/liquid ratio, and particle size by diffusion; and wherein said device has a total footprint area less than about 0.25 m$^2$, an elevation less than about 0.45 m, a weight less than 20 kg, and an operating power demand less than 500 W.

2. The device according to claim 1 wherein the characteristic of the phases or particles being measured is the total surface area.

3. The device according to claim 1 wherein the total footprint area is less than 0.2 m$^2$, the maximum elevation is less than 0.3 m, and the operating power demand is no more than 150 W.

4. The device according to claim 1 wherein the NMR probe module, the means for generating radio frequency and magnetic field gradient pulses, the signal processor and the master controller are integrated into a single cabinet having a total footprint area less than about 0.25 m$^2$, an elevation less than about 0.45 m, a weight less than 20 kg, and an operating power demand less than 500 W.

5. The device according to claim 4 wherein the cabinet has a total footprint area less than about 0.2 m$^2$, the maximum elevation is less than about 0.3 m, and the operating power demand is no more than about 150 W.

6. The device according to claim 1 wherein the NMR probe module comprises a magnet and yoke assembly having adjustable faces, said magnet maintaining a magnetic field directed across the chamber having a field strength between 0.2 and 0.5 Tesla and a magnetic field inhomogeneity of less than 1 part in 10$^3$ over a sample volume of 1.0 cm$^3$; a means for transmitting radio frequency pulses and detecting magnetic response from the dispersion; and a means for transmitting magnetic field gradient pulses.

7. The device according to claim 6 wherein the yoke assembly has 3-fold symmetry and is comprised of three arms fitted with adjustable alignment screws.

8. The device according to claim 6 wherein the magnet comprises samarium cobalt or neodymium-iron-boron.

9. The device according to claim 6 wherein the magnet is an electromagnet.

10. The device according to claim 1 wherein the pulse generator comprises a selectable means for generating a radio frequency pulse of about 10 W up to about 200 W to a sample volume of 1.0 cm$^3$ at frequencies between about 1 and about 20 MHz over a duration of about 5 to about 20 µs; and a selectable means for generating a magnetic field gradient pulse that generates a magnetic field gradient across a sample volume of up to 1.0 cm$^3$ of up to about 1 Tm$^{-1}$.

11. The device according to claim 1 wherein the master controller comprises a field programmable logic array capable of timings accurate to better than +/−1 microsecond and providing RF pulses of about 1 µs to about 1000 µs with rise and fall times less than 1 µs, and sequence pulsing having a step size less than 0.1 µs with 0, 90, 180, and 270 degree phase shifts.

12. The device according to claim 1 wherein the radio frequency pulses are generated by the discharge of one or more capacitors.

13. The device according to claim 1 wherein magnetic response detecting means is sensitive to 10$^{-6}$ Tesla over a length of 5 mm.

14. A method of using the portable device according to claim 1 to measure the surface area and/or particle size and/or volume fraction of liquid of a dispersion comprising finely divided liquid, gas, or solid particles dispersed in a fluid phase.

15. The device according to claim 1 that further provides a user with a series of predetermined actions or steps through hard-wired or software algorithms whereby the measurement of one or more characteristics of the phases or particles comprising the dispersion selected from the group consisting of surface area, solid/liquid ratio, particle size, and elemental analysis is accomplished according to a set protocol.

16. A method for determining the atomic concentration of Lithium, Fluorine, or Phosphorus from the signal intensity of the device of claim 1.

17. A method for determining surfactant adsorption isotherms from the measured NMR relaxation rate constants using the device of claim 1.

18. A method for determining the in-situ surface area of particles dispersed in a liquid using low field NMR relaxation times, said method comprising the steps of:
   i) determining an average NMR relaxation rate constants, $R_1^{ave,ref}$ or $R_2^{ave,ref}$, of one or more reference dispersions having known total particle surface area per unit volume of liquid, $A_T^{ref}$;
   ii) computing the proportionality constant, $k_{AL}$, for the reference dispersion from the equation, $R_n^{ave,ref} = k_{AL}^{ref} A_T^{ref}$; where n=1 or 2;
   iii) determining an average NMR relaxation rate constants $R_1^{ave,sample}$ or $R_2^{ave,sample}$ of a sample dispersion whose surface area is to be determined;
   iv) computing the total surface area of the sample dispersion, $A_T^{sample}$ from the equation, $R_n^{ave,sample} = k_{AL}^{ref} A_T^{sample}$, where n=1 or 2, and
   v) measuring and obtaining the relaxation times from the NMR output data stored in computer hardware using computational steps i)- iv) to determine the in-situ surface area of particles dispersed in a liquid of said in-situ surface.

19. The method according to claim 18, wherein the relaxation times are measured with the device of claim 1.

* * * * *